United States Patent
Magne Ortega et al.

(10) Patent No.: US 6,874,366 B2
(45) Date of Patent: Apr. 5, 2005

(54) SYSTEM TO DETERMINE AND ANALYZE THE DYNAMIC INTERNAL LOAD IN REVOLVING MILLS, FOR MINERAL GRINDING

(75) Inventors: Luis Alberto Magne Ortega, Santiago (CL); Waldo Marcelo Valderrama Reyes, Viña Del Mar (CL); Jorge Antonio Pontt Olivares, Viña Del Mar (CL); Ennio Carlo Perelli Bacigalupo, Viña Del Mar (CL); Claudia Paola Velasquez Lambert, Santiago (CL); German Arnaldo Sepulveda Villalobos, Valpariso (CL)

(73) Assignees: FFE Minerals Corporation, Bethlehem, PA (US); Universidad Technica Federico Santa Maria (CL); Faeta Maria Universidad de Santiago de Chile (CL)

(*) Notice: Subject to any disclaimer, the term of this patent is extended or adjusted under 35 U.S.C. 154(b) by 0 days.

(21) Appl. No.: 10/769,660

(22) Filed: Jan. 30, 2004

(65) Prior Publication Data

US 2004/0255680 A1 Dec. 23, 2004

(30) Foreign Application Priority Data

Jan. 31, 2003 (CL) .............................. 189-2003

(51) Int. Cl.[7] .............................. G01N 29/00
(52) U.S. Cl. ................ 73/649; 73/7; 73/644; 73/660

(58) Field of Search .................. 73/649, 1.15, 1.16, 73/1.89, 7, 593, 657, 660, 781, 789

(56) References Cited

U.S. PATENT DOCUMENTS

| | | | | |
|---|---|---|---|---|
| 4,722,485 A | * | 2/1988 | Young et al. | 241/179 |
| 6,276,210 B2 | * | 8/2001 | Kiuchi et al. | 73/622 |
| 6,314,788 B1 | * | 11/2001 | Williams, Sr. | 73/7 |
| 6,341,525 B1 | * | 1/2002 | Takada et al. | 73/627 |
| 6,446,509 B1 | * | 9/2002 | Takada et al. | 73/627 |
| 6,510,729 B2 | * | 1/2003 | Bonnevie et al. | 73/86 |
| 6,615,670 B2 | * | 9/2003 | Shibasaki et al. | 73/781 |
| 6,739,207 B2 | * | 5/2004 | Sjoquist | 73/864.81 |
| 6,769,957 B2 | * | 8/2004 | Buttram | 451/5 |

* cited by examiner

Primary Examiner—Hezron Williams
Assistant Examiner—Jacques M. Saint-Surin
(74) Attorney, Agent, or Firm—Daniel De Joseph (57) ABSTRACT

A system and method of directly, dynamically and on-line measuring different parameters related to the volume dynamically occupied by the internal load of rotating mills when in operation; specifically, an on-line measurement of the total dynamic volumetric load filling, dynamic volumetric ball load, dynamic volumetric mineral filling and of the apparent density of the internal load of the mill. The present invention comprises a series of wireless acoustic sensors attached to the mill's outer body, a receiving and/or conditioning unit located near the mill, a processing unit and a communication unit.

40 Claims, 10 Drawing Sheets

SYSTEM TO DETERMINE AND ANALYZE THE DYNAMIC INTERNAL LOAD IN REVOLVING MILLS, FOR MINERAL GRINDING

CLAIM OF PRIORITY

This application claims foreign priority under 35 U.S.C. 119(a) from Chilean Application No 189-2003, filed Jan. 31, 2003.

FIELD OF THE APPLICATION

The present invention refers to mineral grinding. Specifically it refers to a system and method of directly on-line measuring the variables of a grinding process, and more specifically to a system for determining and analyzing the internal dynamic load of Revolving Mills.

DESCRIPTION OF THE PRIOR ART

Mineral grinding is a relevant process in metal production. This process is generally carried out with large rotating mills, which use free steel balls inside them as grinding means, to facilitate the transfer of mechanical energy for wearing and fracturing the mineral. The inner-walls of mills are lined with replaceable steel pieces called "lining", which useful life greatly depends on the proper handling of the load, comprised of mineral, grinding means and water. These mills are referred to as semi-autogenous (SAG) mills.

Existing grinding systems have disadvantages, which prevent them from being more efficient, not only because of the lining's short useful life, subject to such aggressiveness that there is accelerated wear of the mill's grinding means and lining, causing a sub-utilization of the grinding mill capacity, as well as periodical shut-downs and repairs, increasing the cost of the metal grinding production line.

A relevant aspect on the control of these mills has been knowing the volumetric filling of the internal load (mineral and/or balls), for which different methods of indirect determination have been traditionally applied using the oil pressure of the different bearings supporting them (PSI). The use of the PSI generates great errors due to the dependency of it on such factors as temperature, oil viscosity, mill speed, position of the load inside the mill, etc.

None of existing systems performs a direct and on-line measurement of the parameters related to the movement and composition of the load in revolving mills, which, in turn, allows for the optimization of the grinding process and increase in mill availability.

The systems and methods that are currently used in mills indirectly consider these parameters from supposed correlations with other variables of the process. For example, the total volumetric load filling is correlated with the pressure of the bearings, a value that can vary with mill speed, lining wear, temperature and proportion between the total volumetric filling and the volumetric ball load.

On the other hand, measuring the volumetric ball load generally requires dumping existing mineral into the mill and then stopping in order to make visual inspections of existing ball content. This operation takes around one hour, causing a substantial production loss.

In the first half of the past century there was invented a device for determining the fill level of mills which was comprised of a microphone that only detected the general intensity of the acoustic noise near the mill, without distinguishing whether this noise was caused by impacts, noise from the natural overturning of the load or from an external and independent source, its output only being a current signal to the plant's control system.

Another device, referred to as the "On-line load angle stimulator", developed by the Chilean Research Center for Mining and Metallurgy (CIMM), uses a sensor attached to the mill shell, that applies the load angle principle to determine the volumetric load filling. Its working principle consists in determining the load angle from the sound generated and inferring the volumetric load filling by assuming that there exists a correlation between both variables. This load angle estimate is a simple and idealized approximation of the internal behavior of the load, since it does not reflect the actual behavioral profile of the load inside the mill when revolving at regular operational speeds.

BRIEF DESCRIPTION OF THE INVENTION

The present invention consists of a system and method of directly, dynamically and on-line measuring different parameters relating to the volume dynamically occupied by the internal load of revolving mills, when in operation. The invention is mainly comprised of a series of wireless acoustic sensors attached to the mill, a receiver and/or conditioning unit located near the mill, a processing unit and a communications unit. The system's output variables are transmitted to the plant's control system, data that may be used by it automatically or manually.

Therefore, an objective of the present invention is to increase efficiency in the grinding process and mill availability through on-line measurement of the volumetric filling of the total dynamic load, volumetric dynamic ball load, volumetric dynamic mineral filling and apparent density of the mill's internal load.

Another purpose of the present invention is to allow monitoring the location, in real time, of the load foot, which corresponds to the estimated position where the lifters contact the moving load, and of the load shoulder, which corresponds to the location where the load starts to fall onto the load foot, in addition to the values determined by the system and most relevant data.

Another objective is to stabilize mill operation by adding new knowledge to decision making relating to control, which allows to increase average processed tonnage, decrease operational singularities stoppages, oscillations in filling level, inspection of lining, etc., and, in time, optimum use of the electricity that powers the mill's motor, and the adequate handling of the load movement.

DETAILED DESCRIPTION OF THE PREFERRED EMBODIMENTS

Figure 1:
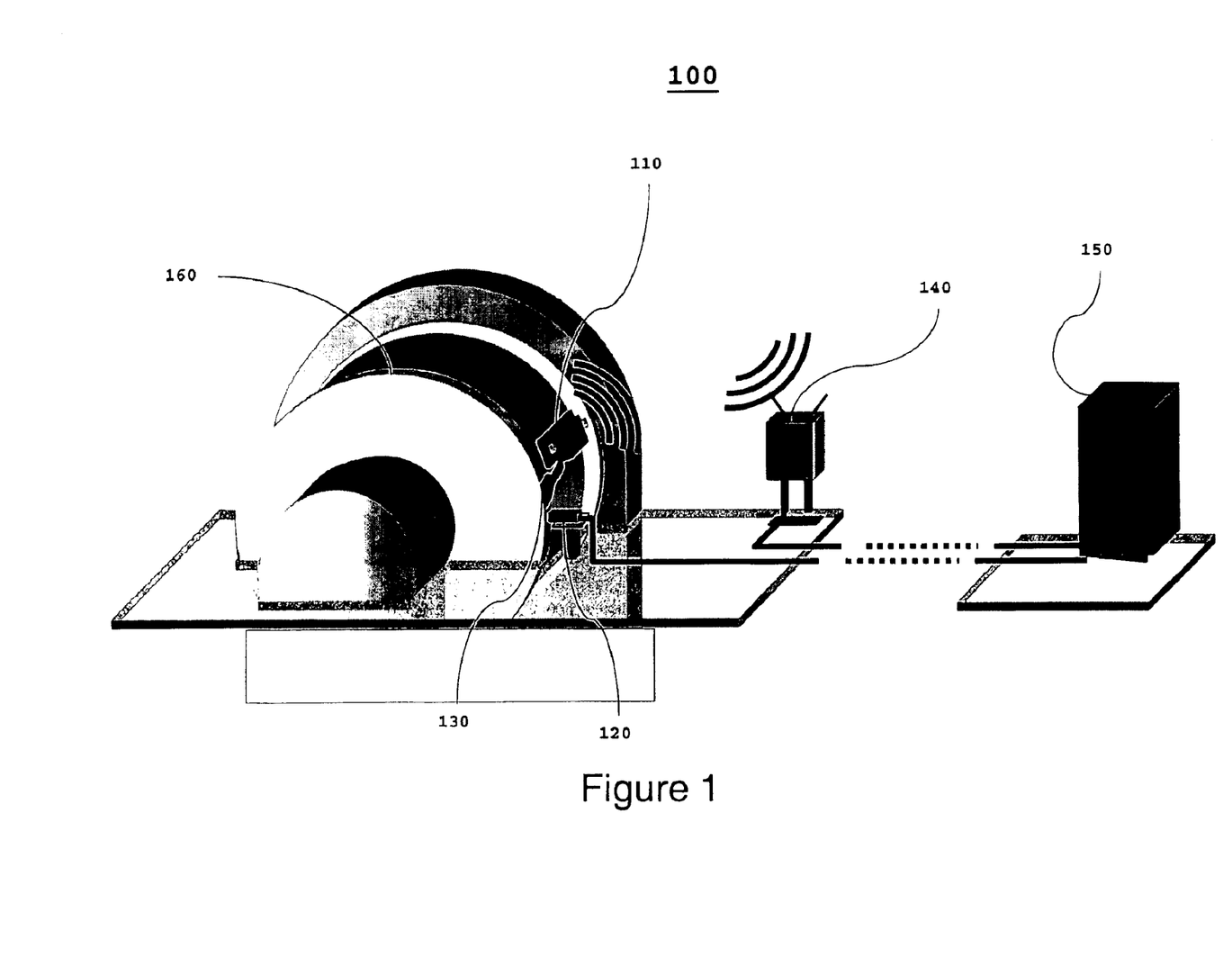
FIG. 1 is a schematic and simple description of the system of the present invention.

FIG. 1 describes a preferred embodiment of the present invention, in a system 100, a SAG mill 160 has on its outer shell a mechanically fastened wireless acoustic sensor 110 that detects and transmits via a radio signal the sound generated from the interior of SAG mill 160; on a side is a synchronism sensor 120 that is able to detect the passing of metallic element 130 conveniently attached to the mill shell and to transmit a synchronism signal to identify the angular position of the wireless acoustic sensor 110 to a receiver 140 that receives the signals transmitted by sensor 110; a processing and control means 150 receives the signals transmitted by receiver 140 and synchronism sensor 120 for processing the variables of system 100.

Figure 2:
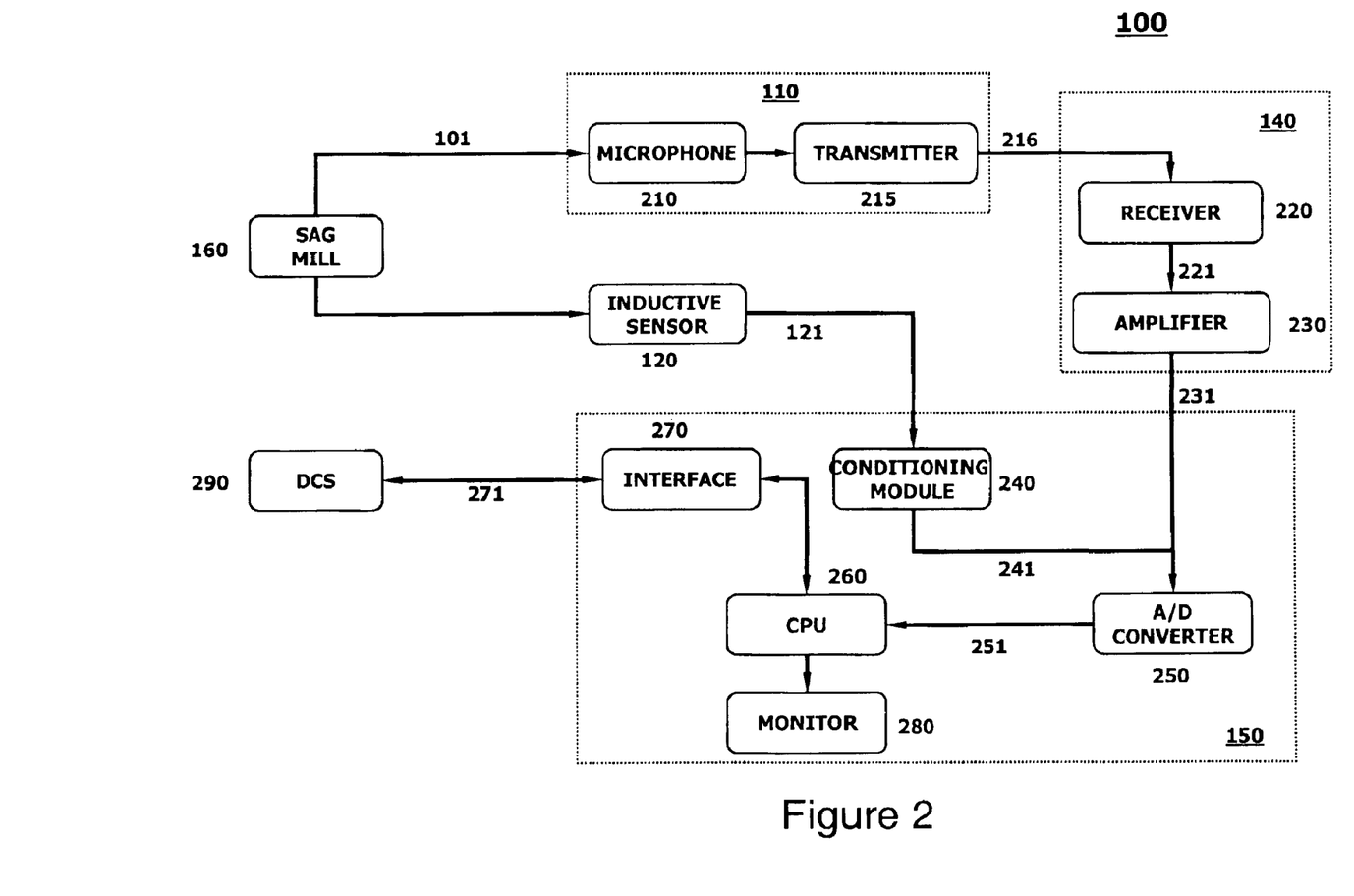
FIG. 2 is a general block diagram of the system of the present invention.

FIG. 2 describes a block diagram of the electric means comprising system 100 of the present invention. The sound 101 produced inside the mill is captured by an acoustic microphone 215, signal 216 is transmitted by transmitter 215 and is received by receiver 220 that delivers a signal 221 to amplifier 230, which in turn sends out an analog signal 231 to processing and control unit 159, which contains an analog to digital signal converting unit 250. The synchronism sensor 120 produces a first synchronism signal 121 to determine the relative position of sensing means 110. The processing and control unit 150 receives the signal from the synchronism signal 121, which is processed by a conditioning module 240 that transmits a second synchronism signal 241 to the analog to digital signal converting unit 250. The analog to digital signal converting unit 250 delivers a digital signal to a CPU 260 that runs an input/output interface means 270 necessary to allow bi-directional communication 271 that may be either analog or digital, with the DCS plant's control system 290. In addition, it has display means 280 allowing to see in real time the values determined by the system 100 and most relevant operational data.

Figure 3:
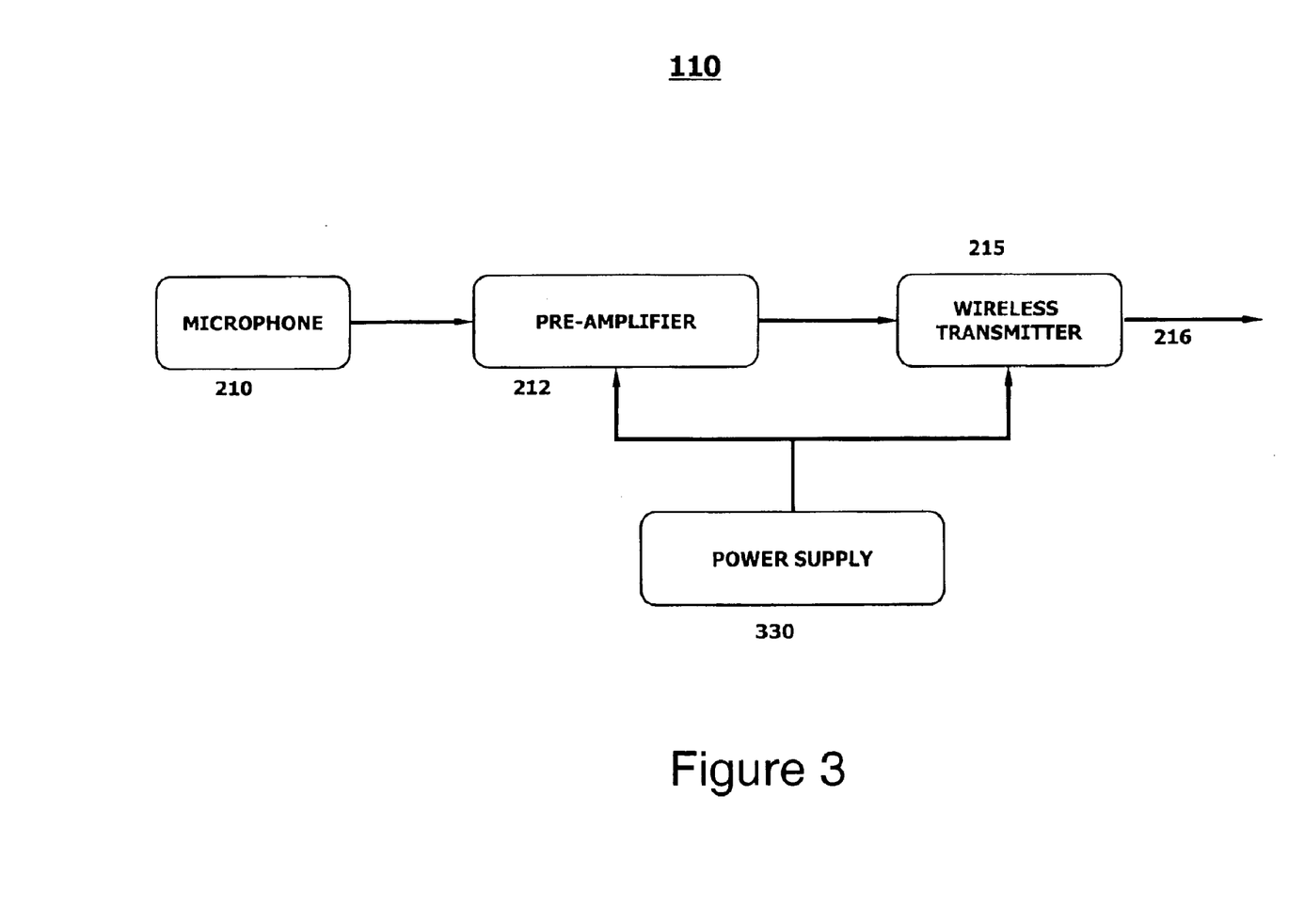
FIG. 3 is a block diagram of the wireless acoustic sensor.

FIG. 3 is a block diagram of wireless acoustic sensor 110, which is comprised of at least one microphone 210, a pre-amplifier 212, a wireless transmitter 215 and a power supply 330, all encased in a metallic two-compartment casing (not shown), suitable to environmental and mechanical conditions, mounted on the mill's shell through an insulating system provided with means to decrease the effect of vibrations. Microphone 210 may be active (with pre-amplifier 212) or passive, and adequate to withhold the sound intensity coming from the mill, which is acoustically insulated within acoustic sensor 110, being supported by a rubber structure intended to reduce the effect of acoustic and mechanical vibrations on the performance of the microphone 210.

Figure 4:
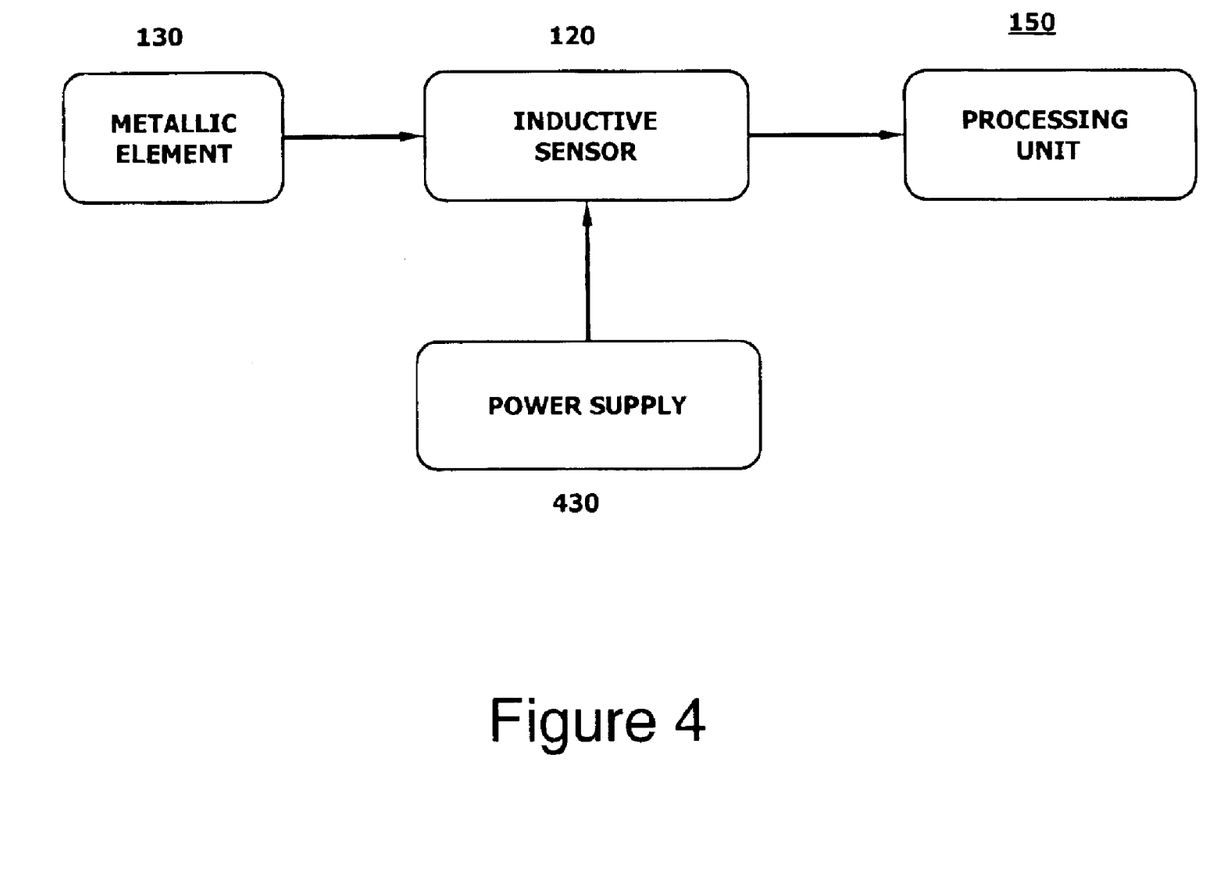
FIG. 4 is a block diagram of the inductive sensor.

FIG. 4 shows a block diagram of synchronism sensor 120, fed by a power supply 430 that transmits a referential position signal 121; the synchronism sensor may be of a capacitive or optical type, preferably inductive, conveniently located to detect the passing of a metallic element 130 attached to the shell, with each revolution of the mill, even being the same acoustic sensor 110 the one being detected. Pulse 121 generated by each revolution of the mill is sent to the processing and control unit 150 through the conditioning unit and A/D converter 250.

Transmitter 215 may be of digital or analog technology and may operate on microwave bands, UHF or VHF, as necessary, preferably a high-fidelity UHF transmitter.

Power supply 330 may be batteries, for which NiMH rechargeable, Ion-polymer cells or multi-cell batteries are used to achieve a 45-day minimum autonomy. In addition, it also has a voltage regulator maintaining a constant voltage for transmitter 215. This power supply may have associated therewith an external charge system, which is used to recharge the batteries once their capacity has exhausted. This system (not shown) is comprised of independent load circuits in equal number to the number of cells used. It comprises a load control by current and by voltage and temperature and maximum charge time protections.

The load system may also be an internal one, and be auto-generation based, having a intermediate accumulator, through a pendulum dynamo and generator, making use of the mill spinning, or through a magnetic generator, making use of the induction from the magnetic field, present in the vicinity of the mill, as a loop arrangement that revolves together with the mill or through another mechanism transforming the mill vibrations into electric power.

Figure 5:
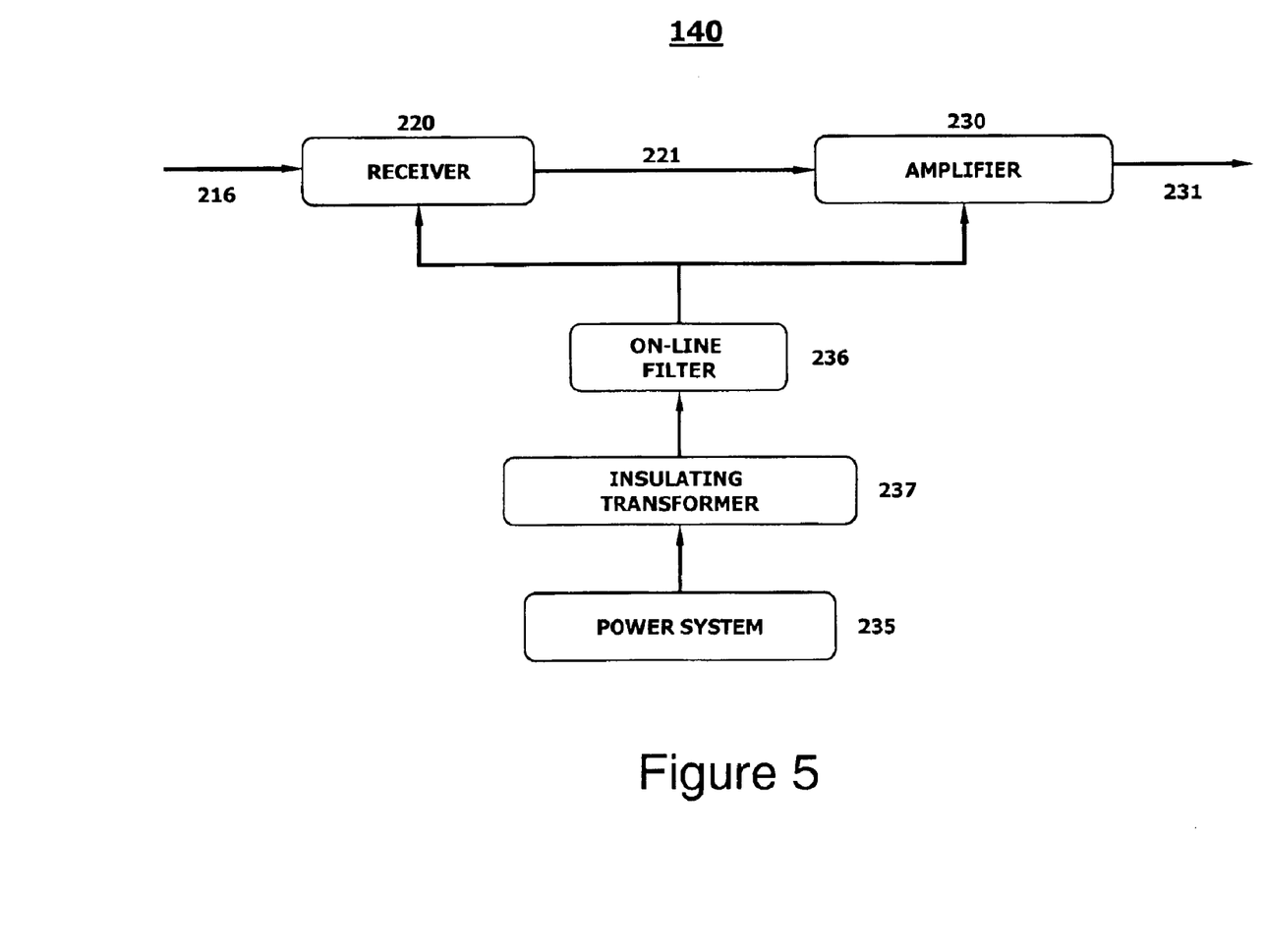
FIG. 5 is a block schematics of the receiver.

FIG. 5 describes, by way of a block diagram, receiver 140, that performs the reception and reconditioning of the signals 216 delivered by the transmitter 215 and transformed into an electric signal 231 that may be transmitted, via cable, to the processing and control unit, and which use the same technology as that of the transmitter (A/D and microwaves, UHF or VHF). In some cases, and depending on the distances involved, this block may be next to the processing and control unit. It is powered by the power system (110 or 220 VAC, 50 or 60 Hz), which is conditioned by a line filter 236 and an insulating transformer 237 to eliminate the potential high-frequency electric noise inherent to the application. In addition, a signal conditioning stage, to transform it into a voltage signal, a current signal or an optic signal, may be incorporated.

Figure 6:
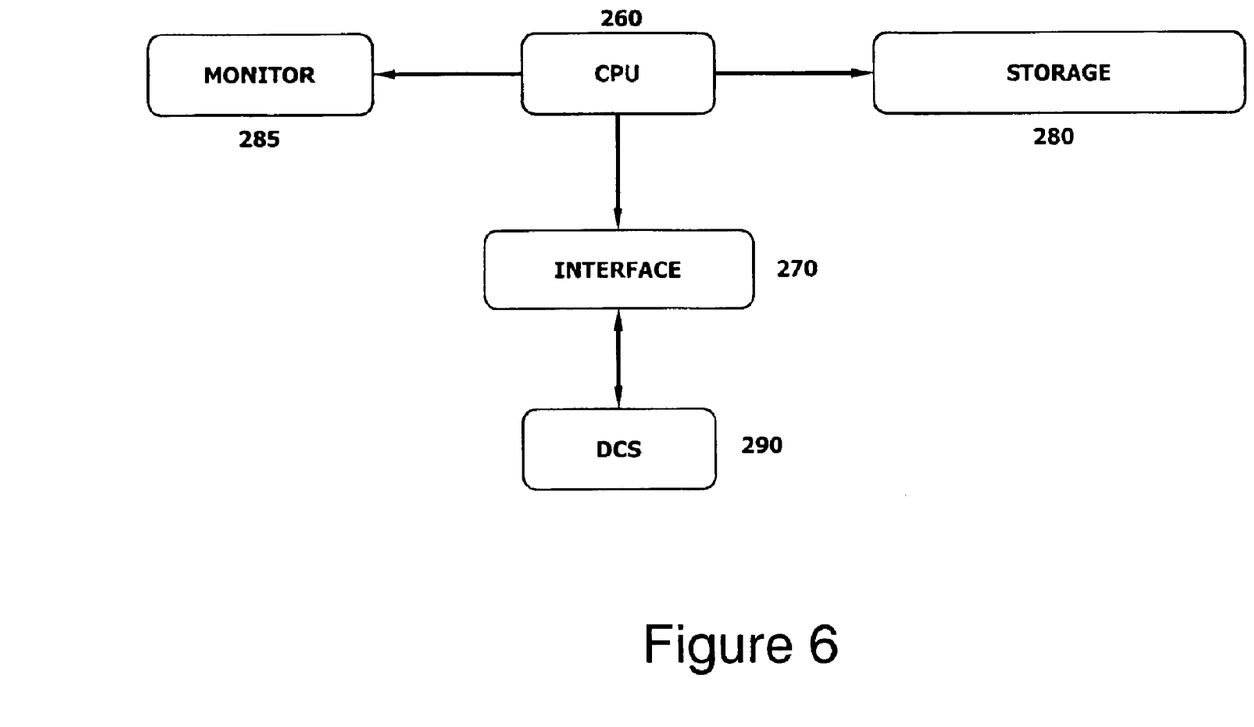
FIG. 6 is a block diagram of the processing unit.

FIG. 6 describes the CPU 260 and the I/O interface means 270 necessary to allow bi-directional communication with the plant's control system 290 (DCS, to read the process data required for the different operational methods of system 100). In addition, CPU 260 sends to the DCS the results produced by system 100. Its composition depends on each particular plant, but it may contain serial communications modules (RS-232, RS-485, RS-422, etc.) or network communications modules (LAN, TCP/IP, etc.). Further, it is comprised of a data storage means 280, such a HDD or similar, and an information display unit 285, such as a computer monitor. Processing and control block 150 is comprised of an A/D converter 250 and the processing unit as such. Its function is to process acoustic signals 231 and 241 coming from the receiving and conditioning means 140 as well as from the referential position sensor 120, respectively, to determine the load foot and load shoulder angles, the volumetric dynamic load filling, volumetric dynamic ball load, volumetric dynamic mineral filling, and to determine the apparent density of the load. Said processing unit 150 is comprised of some kind of electronic processor, such as a PC, DSP, microcontrollers, microprocessors, etc. In general, it may made up of a computer, either PC or industrial type, or any processing unit from the microprocessor, microcontroller or DSP family.

Figure 7A:
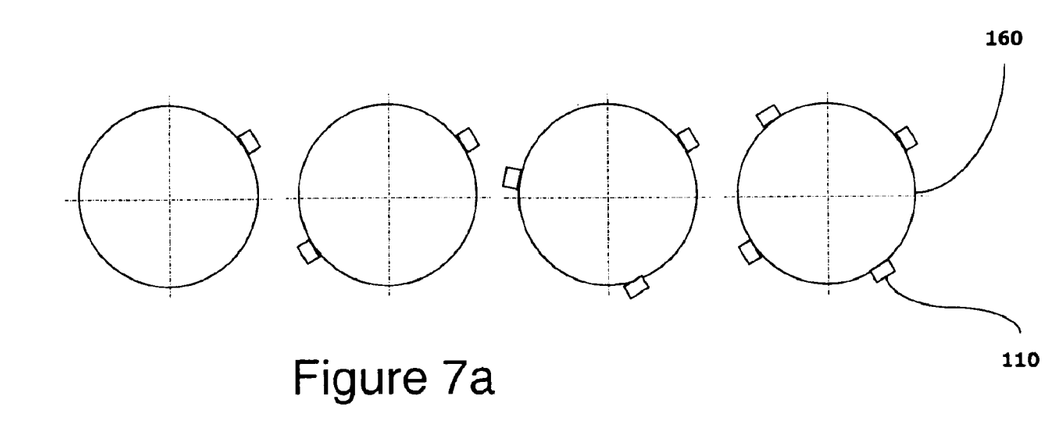
FIGS. 7a and 7b show different embodiments, as to location and distribution, of the acoustic sensors on the mill casing.
Figure 7B:
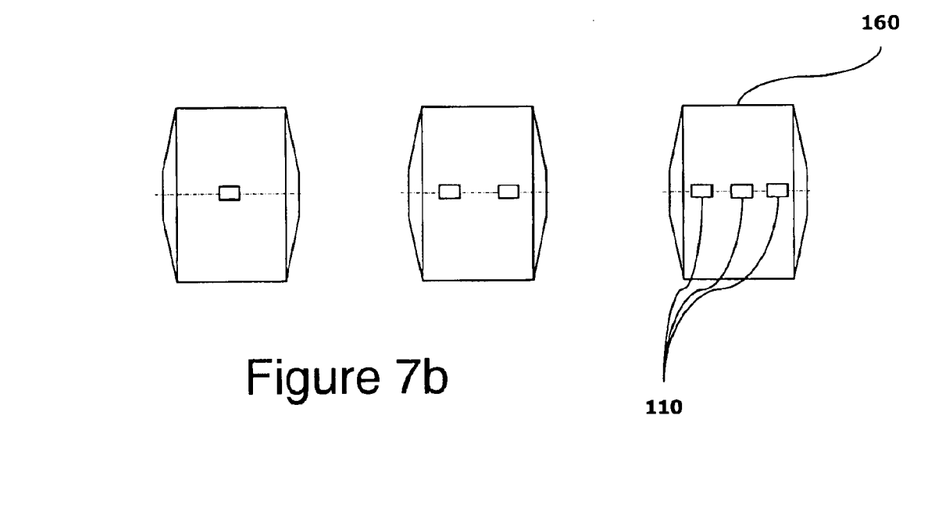

FIGS. 7a and 7b describe possible positions and distributions of system 100, when it has more than one wireless acoustic sensor 110. FIG. 7a shows up to four positions in the perimeter of mill shell 160 for sensors 110. FIG. 7b shows the number of sensors that may be mounted for each one of the positions shown in FIG. 7a; therefore, it is possible to configure the system 100 with a number of acoustic sensors 10, from one sensor to at least 12 sensors arranged as shown in FIGS. 7a and 7b.

Figure 8:
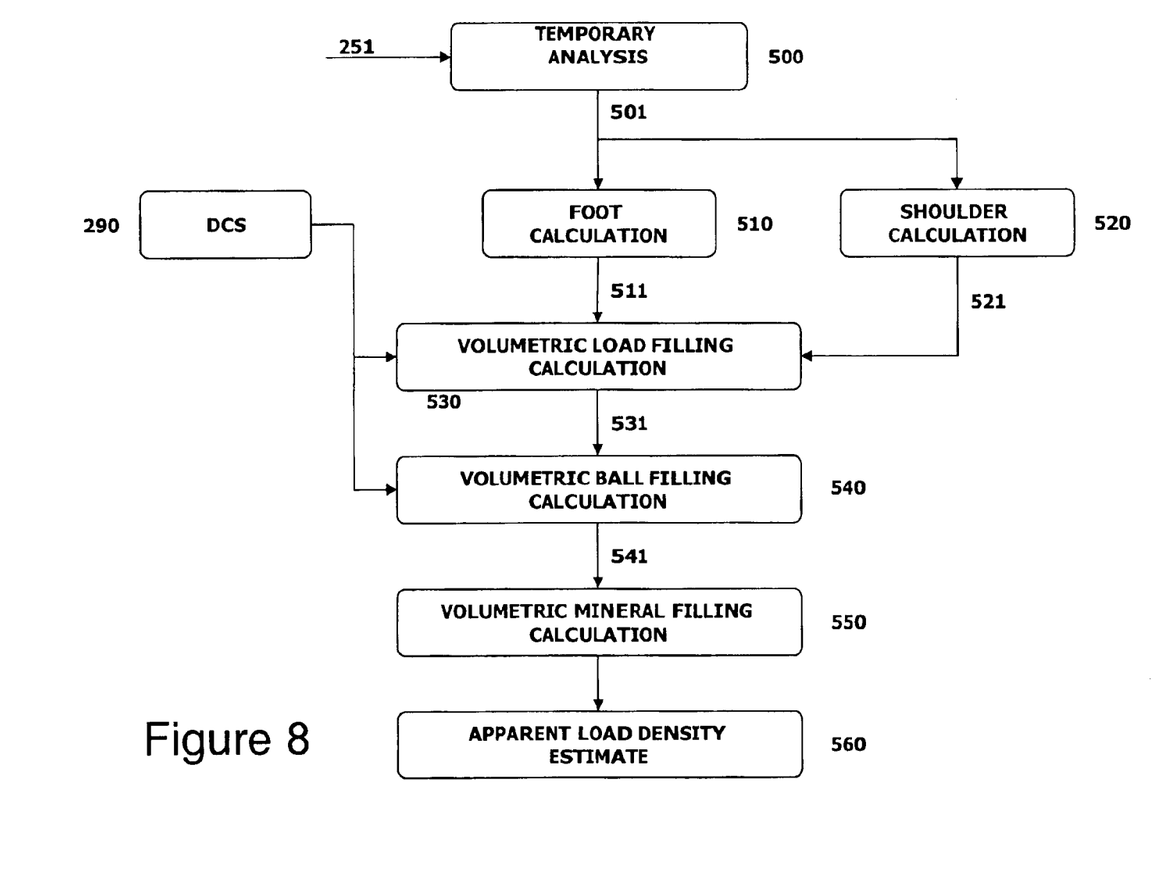
FIG. 8 is a block diagram of the operational method of the present invention.

FIG. 8 shows a block diagram of the operational method of the invention. The digital sound and synchronism pulse signals 251 are temporarily analyzed to determine the sound portion corresponding to a full turn of the mill plus the last fourth of the previous turn and the first fourth of the next turn, the first and last point of the resulting signal 501 coming to zero, thus preventing the edge effects of the previous filtering process. In addition, the zero reference of the angular position of the acoustic sensor 110 is defined based on the synchronism signal, identifying the start and end of a turn and transforming the temporary axis into an equivalent angular axis, assigning the zero degree reference to the mill's vertical position. The operational Foot Calculation 510 and Shoulder Calculation 520 methods take the resulting signal 501 and process it spectrally in order to determine the angle of load foot 511 and the angle of load shoulder 521. Then, the operational method "Calculation of Total Volumetric Dynamic Load Filling" 530 reads from the DCS 290 the necessary operational data, and uses them in conjunction with the load foot angle 511 and the load shoulder angle 521 to calculate the Volumetric Dynamic Load Filling 531. Based of this value and other data from the process, the operational methods make the Calculation of Volumetric Dynamic Ball load 540, the result being the Dynamic Volumetric Ball load 541. With this value and that of the Dynamic Volumetric Mineral Filling 531, the Dynamic Volumetric Mineral Filling 550 is determined as the arithmetic difference between them. Finally, from the Dynamic Volumetric Ball Load 541 and the Dynamic Volumetric Mineral Filling 550 the Apparent Density of load 560 is determined, assuming that the mineral density and the density of the grinding medium (e.g., the balls) is known. Lastly, all the determined values are sent to the DCS 290 and, optionally, to a result visualization display.

Figure 9:
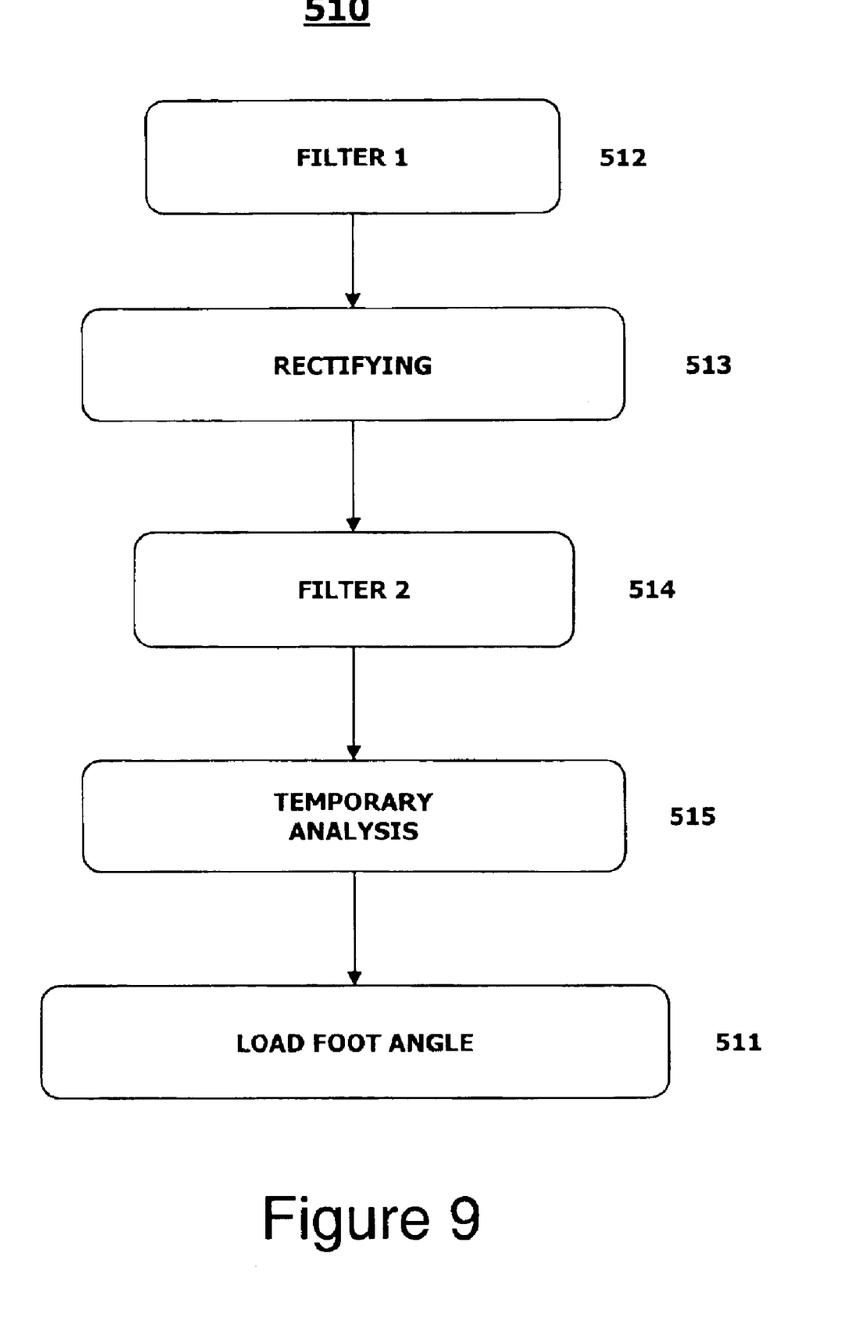
FIG. 9 is a block diagram of the load foot determination stage of the operational method of the present invention

FIG. 9 shows the operational method of calculating the load foot angle. The resulting signal 501 is applied a digital high-pass filter with a cut-off frequency at 2 or 3 Hz, of 6th order and with phase correction 512. Phase correction is made through a double-filtering procedure, applying a filter on the original data and then another filter, with identical characteristics, to the filtered signal, but reverting the direction of the signal. Then, the resulting signal's envelope using a rectified process 513 (absolute value) and filtered at low frequency 514. Maximum width is found in the envelope and the relative angular position of the angular axis is obtained, thus being defined the absolute angular position of the load foot with respect to the mill's vertical position.

Figure 10:
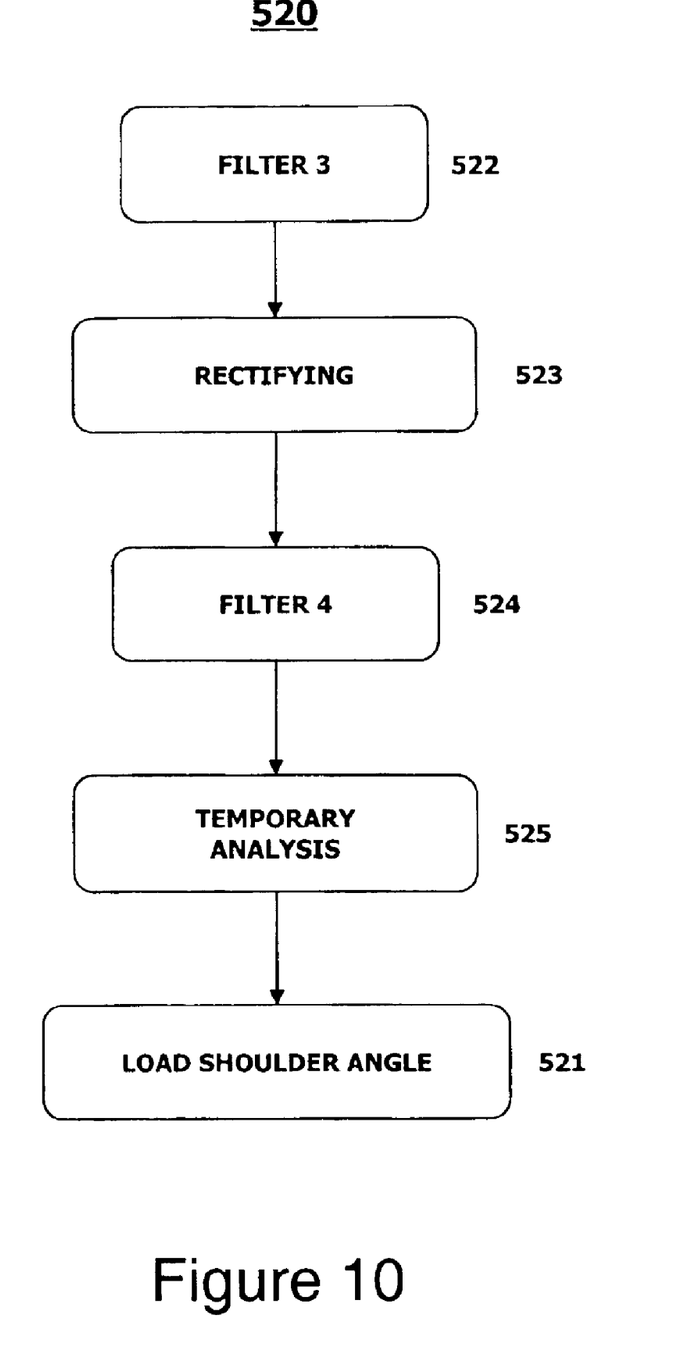
FIG. 10 is a block diagram showing the load shoulder determination phase of the operational method of the present invention.

FIG. 10 shows the operational method of determining the angle of the load shoulder. The resulting signal 501 is applied a digital band pass filter with shut-off frequencies at 180 and 400 Hz, of 6th order, and with phase correction 522. Phase correction is made through a double-filtering procedure, applying a filter on the original data and then another filter, with identical characteristics, to the filtered signal, but reverting the direction of the signal. Then, the resulting signal's envelope using a rectified process 523 (absolute value) and filtered at low frequency 524. Maximum width is found in the envelope and then the first minimum for, from there, look for the maximum positive grade before reaching the mill vertical. Then the absolute angular position of the load shoulder obtained, from the angular axis of the original signal.

The volumetric filling of the total dynamic load $J_C$ is obtained from the position of the internal load foot $\theta_P$ and shoulder $\theta_H$ of the load, and from the revolving speed expressed as the critical speed fraction $\phi_C$. The equation used is as follows:

$$J_C\% = \frac{\pi + A \cdot \theta_P \cdot (B + C \cdot \phi_C) - D \cdot \phi_C \cdot \theta_H}{E \cdot \theta_P}$$

where A, B, C, D and E are constants that are determined experimentally during the system start-up and calibration stages through various visual inspections of the condition of the load inside the mill. In general, they depend on constructive and operational aspects of the mill and on the degree of lining wear. The visual inspections consists in geometrically measuring the volume occupied by the total load when the mill is idle, from which it is possible to determine the volumetric filling relative to the mill's total volume. With the data obtained from the different inspection a procedure to minimize mean quadratic error to obtain the value of each constant is carried out.

The dynamic volumetric ball load $J_B$ is obtained from the total volumetric load filling $J_C$ as determined by the system, of the operational variables inherent to the process obtained from the plant's control system, such as power, feed water flow, feed mineral flow, speed, processed tonnage, time of operation, and from characteristic parameters related to grinding means, from the mineral and from the mill itself. The system stores the aforementioned values in each calculation cycle for $J_C$, which generally takes place every 15 seconds. Once a period of about one hour has elapsed, the system performs an mean quadratic error minimization analysis in the interactive determination on the power consumed by the mill, variable that is read from the plant's control system and therefore known, delivering, as a result, the value of $J_B$ where the error is minimum.

Below is detailed the set of equations used in the process, consisting of empirical adaptations of known theoretical models (Steve Morrel and Fred Chester Bond's power models):

The basis for calculating ball load level $J_B$ is the power consumed by the mill, described through the equation:

$$Pot = A_1 \cdot J_B \cdot K_P \cdot F_V \cdot F_D \cdot F_C$$

where $J_C$ is the total dynamic filling as determined above. Pot is the instantaneous electric power consumed by the mill and $A_1$ is a constant that is determined experimentally during the system start-up and calibration stages through visual inspections of the condition the load inside the mill. In general, speed factor $F_V$ is calculated from the equation:

$$F_V = \phi_C \cdot \left(1 - \frac{0.1}{2^{(9-10 \cdot \phi_C)}}\right)$$

The design factor $F_D$ is determined through the equation:

$$F_D = d_{eff}^{2.5} \cdot L_{mol}$$

where $d_{eff}$ is the mill's mean diameter that is effectively used in the grinding process, value that varies in time and depends on the processed tonnage accumulated by the mill. $L_{mol}$ equals the mill's effective length.

Internal load factor $F_C$ is calculated by using the equation:

$$F_C = 1 - A_2 \cdot J_C$$

where $A_2$ is a constant that is determined experimentally during the system start-up and calibration stages through visual inspections of the condition the load inside the mill.

Power constant $K_P$ is determined experimentally during the system start-up and calibration stages through various visual inspections of the condition the load inside the mill, particularly from the inspection of the volumetric filling that uses balls after a mill wash procedure.

The visual inspections to determine constants $A_1$, $A_2$ and $K_P$ are obtained from geometrical measurements of the volume used by the balls when the mill is stopped. In this case, the mineral inside the mill is discharged prior to stoppage, a procedure that is normally called "grind-out" and is used in most grinding plants. With the data obtained from the different visual inspections, and mean quadratic error minimization procedure is performed to obtain the value of each constant.

With the values of the Dynamic Volumetric Ball load and Dynamic Volumetric Load Filling, the Dynamic Volumetric Mineral Filling is determined as the arithmetic difference between them. Finally, based on the Dynamic Volumetric Ball load and Dynamic Volumetric Mineral Filling Apparent load Density is determined as a coefficient between the total mass of the load and the Dynamic Volumetric Load Filling. The total mass of the load is the sum of the mineral mass and the ball mass, assuming that the density of the mineral as well as that of the balls are known constants.

The display means represent, graphically and numerically, the results produced by the system. Optionally, these means may also be used for the configuration of the system's parameters.

While there are shown and described present preferred embodiments of the invention, it is distinctly to be understood that the invention is not limited thereto, but may be otherwise variously embodied and practiced within the scope of the following claims.

We claim:

1. A system to determine and analyze the dynamic internal load in rotating mills, for mineral grinding, the system comprising:
   (a) wireless acoustic sensing means to detect sound inside the mill during operation and attached to the shell or external casing of said revolving mill;
   (b) synchronism sensing means to synchronize the revolving movement of the mill and
   (c) processing and control means to:
      (i) determine the load foot angle, corresponding to the estimated position where the lifters contact the load in motion;
      (ii) determine the load shoulder angle, which corresponds to the location where the load or load cataract starts to fall towards the load foot; and
      (iii) determine on-line the volumetric filling of the dynamic load, when the mill is operating.

2. The system of claim 1, wherein the rotating mill uses steel balls as a grinding means.

3. The system of claim 2, wherein the processing and control means further determines the volumetric filling of grinding balls.

4. The system of claim 3, wherein the processing and control means further determines the apparent density of the load.

5. The system of claim 4, wherein the synchronism sensing means is of an inductive type.

6. The system of claim 4, wherein the synchronism sensing means is of a capacitive type.

7. The system of claim 4, wherein the synchronism sensing means is of an optical type.

8. The system of claim 1, wherein the synchronism sensing means detects an element attached to the mill shell or outer body at each turn of the mill.

9. The system of claim 8, wherein said element attached to the mill shell is contained in at least one wireless acoustic sensing means.

10. The system of claim 9, wherein said at least one wireless acoustic sensing means are arranged in at least one group on the mill shell.

11. The system of claim 10, wherein said at least one wireless acoustic sensing means are arranged in two groups on the outer circumference of the mill shell, and are circumferentially spaced at about 180° from each other.

12. The system of claim 10, wherein at least one said wireless acoustic sensing means are arranged in three groups on the outer circumference of the mill shell, and are circumferentially spaced at about 120° from each other.

13. The system of claim 10, wherein at least one said wireless sensing means are arranged in three groups on the outer circumference of the mill shell, and are circumferentially spaced at about 90° from each other.

14. The system of claim 10, wherein each group is made up of at least one wireless acoustic sensor.

15. The system of claim 14, wherein each group is arranged on the mill shell according to its longitudinal axle.

16. The system of claim 15, wherein the wireless acoustic sensors are fed by a power supply connected to an external power supply that is used to recharge the battery cells once their capacity has exhausted.

17. The system of claim 16, wherein the external power supply is comprised of two independent charge circuits of the same number as the number of cells used, and has charge control by current, voltage, and maximum charge temperature and time protections.

18. The system of claim 16, wherein the charge system is internal and based on auto-generation, with an intermediate accumulator, through a pendulum-type generator and a dynamo, making use of the mill's revolving.

19. The system of claim 16, wherein the charge system is internal and based on auto-generation, with an intermediate accumulator, through a pendulum-type generator and a dynamo making use of the induction from the magnetic field present around the mill, as a loop arrangement revolving along with the mill.

20. The system of claim 1, wherein the wireless acoustic sensing means further comprises a means of transmission to transmit a signal.

21. The system of claim 20, further comprising wireless receiving means for said signal.

22. The system of claim 21 wherein the processing and control means receive a signal from the receiving means and a signal from the synchronism sensing means, where the receiving means sends an analog signal to said processing and control means, which signal is received at an analog-to-digital signal converting unit; the synchronism sensing means generating a first synchronism signal to determine the relative position of the wireless acoustic sensing means; the processing and control means receive said first synchronism signal from the synchronism sensor, which first synchronism signal is processed by a conditioning module that transmits a second synchronism signal to said analog to digital signal converting unit, that transmits a digital signal to a CPU that runs an input/output interface means necessary to allow bi-directional communication that may be either analog or digital, with the mill's control system.

23. The system of claim 22, further comprising display means allowing to view, in real time, the estimated values.

24. A method of determining and analyzing the internal dynamic load in revolving mills, for mineral grinding, said method comprising the following steps:
   (a) detecting sound inside the mill, through wireless acoustic sensors attached to the shell of the revolving mill, to thereby provide a sound signal;

(b) providing a synchronism signal to synchronize the revolving motion of the mill; and (c) processing said sound signal and said synchronism signal for:

(i) determining the load foot angle corresponding to the estimated position where the lifters contact the load in motion;

(ii) estimating the load shoulder angle corresponding to the position where the load or load cataract starts to fall toward the load foot; and (iii) estimating, on-line, the dynamic volumetric load filling when the mill is operating.

25. The method of claim 24, wherein the revolving mill uses steel balls as grinding means.

26. The method of claim 25, wherein the processing step further includes the step of determining the dynamic volumetric filling of the grinding balls.

27. The method of claim 26, wherein the processing step further includes the step of dynamic volumetric mineral filling.

28. The method of claim 27, wherein the processing step further includes the step of estimating the apparent density of the load.

29. The method of claim 28, wherein the step of providing a synchronism signal comprises the step of detecting an element attached to the mill shell each time that said mill turns one revolution.

30. The method of claim 29, wherein the sound detection step also comprises the step of transmitting said sound signal.

31. The method of claim 30, further comprising the step of receiving said sound signal and sending said sound signal as in said processing step.

32. The method of claim 31, wherein the processing step also comprises:

(iv) receiving said sound signal and said synchronism signal;

(v) generating a second synchronism signal to determine the relative position of the wireless acoustic sensing means installed on the shell of the revolving mill;

(vi) processing said signals in a analog-digital converter; and (vii) transmitting a digital signal from said analog to digital converter to a CPU that runs an input/output interface necessary for bi-directional communication, that may be analog or digital, with the mill's control system.

33. The method of claim 32, further comprising a display step allowing the view, in real time, of the determined values.

34. The method of claim 24, wherein the step of determining the load foot angle comprises the following steps:

(i) analyzing the digital sound signals and the synchronism pulse temporarily to determine the sound portion corresponding to a full-turn of the mill plus the last fourth of the previous turn and the first fourth of the next turn, the first and last point of the resulting signal coming to zero, thus preventing the edge effects of the previous filtering process;

(ii) defining the zero reference of the angular position of the acoustic sensor based on said synchronism signal;

(iii) applying to the resulting signal a digital high-pass filter having a cut-off frequency at 2 or 3 Khz, of 6 th order and with phase correction;

(iv) applying a phase correction through a double filter to the original signal and then another filter, with identical characteristics to the filtered signal, but reverting the direction of the signal;

(v) obtaining the envelope of the resulting signal, using a rectifying process (absolute value) and again filtering at low frequency;

(vi) finding in the envelope the maximum width, and (vii) obtaining the relative angular position of the maximum found from the angular axis, being thus defined the absolute angular position of the load foot with respect to the mill's vertical.

35. The method of claim 24, wherein the step of determining the angle of the load shoulder comprises the steps of:

(i) temporarily analyzing the digital sound and synchronism pulse signals to determine the sound portion corresponding to a full turn of the mill plus the last fourth of the previous turn and the first fourth of the next turn, the first and last point of the resulting signal coming to zero, so as to prevent the edge effects of the previous filtering process;

(ii) defining the zero reference to the angular position of the acoustic sensor based on said synchronism signal;

(iii) applying to the resulting signal a digital band pass filter with cut-off frequencies between 180 and 400 Hz, of 6 th order and with phase correction;

(iv) applying phase correction through a double-filtering procedure, applying a filter on the original data and then another filter, with identical characteristics, to the filtered signal, but reverting the direction of the signal;

(v) obtaining the envelope of the resulting signal, using a rectifying process (absolute value) and again filtering at low frequency;

(vi) finding the maximum width in the envelope;

(vii) finding the first minimum of the signal from the maximum found;

(viii) finding the maximum positive grade from the first minimum found and before reaching the mill's vertical; and (ix) obtaining from the angular axis the position of the maximum positive grade, thus defining the angular position of the load shoulder with respect to the mill's vertical axis.

36. The method of claim 24, wherein the step of estimating, on line, the volumetric filling of dynamic load comprises the steps of:

obtaining the value of the angle of load foot $\theta_P$;

obtaining the value of the angle of the load shoulder $\theta_H$;

obtaining the revolving speed expressed as the critical speed fraction $\phi_C$;

obtaining the volumetric filling of the total dynamic load $J_C$ based on the equation:

$$J_C\% = \frac{\pi + A \cdot \theta_P \cdot (B + C \cdot \phi_C) - D \cdot \phi_C \cdot \theta_H}{E \cdot \theta_P}$$

where A, B, C, D and E are constants that is determined experimentally during the system start-up and calibration stages through various inspections of the condition of the load inside the mill, that depend on constructive and operational aspects of the mill and on the wear extent of its lining, wherein said inspections comprise geometrically measuring the volume occupied by the total load when the mill is stopped, and with the data obtained from the different inspections carrying out a quadratic error minimizing procedure to obtain the value of each constant.

37. The method of claim 26, wherein the step of determining the dynamic volumetric grinding ball load comprises the steps of:
(i) determining the volumetric filling of total dynamic load $J_C$;
(ii) calculating the dynamic volumetric ball load $J_B$, based on the equation:

$$Pot = A_1 \cdot J_B \cdot K_P \cdot F_V \cdot F_D \cdot F_C;$$

where: Pot is the instantaneous electric power consumed by the mill;
$A_1$ is a constant that is determined experimentally during the system start-up and calibration stages through inspections of the condition of the load inside the mill;
$F_V$ is the mill speed factor, that is determined based on the equation:

$$F_V = \phi_C \cdot \left(1 - \frac{0.1}{2^{(9-10 \cdot \phi_C)}}\right);$$

$F_D$ is determined by the equation:

$$F_D = d_{eff}^{2.5} \cdot L_{mol};$$

where $d_{eff}$ is the mill's mean internal diameter that is effectively used in the grinding process, having a value that varies in time and depends on the processed tonnage accumulated by the mill;
$L_{mol}$ equals the effective length of the mill;
$F_C$ is the internal load factor calculated through the equation:

$$F_C = 1 - A_2 \cdot J_C;$$

where $A_2$ is a constant that is determined experimentally during the system start-up and calibration stages through inspections of the condition of the load inside the mill; and
$K_P$ is a power constant that is determined experimentally during the system start-up and calibration stages through various inspections of the condition of the load inside the mill, including from the inspection of the volumetric filling that uses balls after a mill wash procedure, where said inspections to determine constants $A_1$, $A_2$ and $K_P$ are obtained from measurements of the volume used by the balls when the mill is stopped, for which the mineral inside the mill is discharged prior to stoppage, and with the data obtained from the different inspections a mean quadratic error minimization procedure is performed to obtain the value of each constant.

38. The method of claim 36, wherein the step of determining the dynamic volumetric filling of grinding balls comprises the steps of:
(i) calculating the total dynamic volumetric load filling $J_C$;
(ii) calculating the dynamic volumetric ball load $J_B$, based on the equation:

$$Pot = A_1 \cdot J_B \cdot K_P \cdot F_V \cdot F_D \cdot F_C;$$

where: Pot is the instantaneous electric power consumed by the mill;
$A_1$ is a constant that is determined experimentally during the system start-up and calibration stages through inspections of the condition the load inside the mill;
$F_V$ is the mill speed factor, that is determined based on the equation:

$$F_V = \phi_C \cdot \left(1 - \frac{0.1}{2^{(9-10 \cdot \phi_C)}}\right);$$

$F_D$ is determined by using the equation:

$$F_D = d_{eff}^{2.5} \cdot L_{mol};$$

where $d_{eff}$ is the mill's mean internal diameter that is effectively used in the grinding process, having a value that varies in time and depends on the processed tonnage accumulated by the mill;
$L_{mol}$ equals the effective length of the mill;
$F_C$ is the internal load factor calculated through the equation:

$$F_C = 1 - A_2 \cdot J_C;$$

where $A_2$ is a constant that is determined experimentally during the system start-up and calibration stages through inspections of the condition of the load inside the mill;
$K_P$ is a power constant that is determined experimentally during the system start-up and calibration stages through various inspections of the condition the load inside the mill, including from the inspection of the volumetric filling that uses balls after a mill wash procedure, where said inspections to determine constants $A_1$, $A_2$ and $K_P$ are obtained from geometrical measurements of the volume used by the balls when the mill is stopped, for which the mineral inside the mill is discharged prior to stoppage, and a mean quadratic error minimization procedure is performed to obtain the value of each constant.

39. The method of claim 27, wherein the step of determining the dynamic volumetric mineral filling is obtained as an arithmetic difference between the dynamic volumetric load filling and the dynamic volumetric ball load.

40. The method of claim 28, wherein the step of determining the apparent density of the load comprises the steps of:
(a) obtaining the mineral mass from the dynamic volumetric mineral filling and the known density of the mineral;
(b) obtaining the ball mass from the dynamic volumetric ball load and the known density of the balls;
(c) obtaining the total mass of the mass as the sum of the mass of the mineral and of the balls; and
(d) obtaining the apparent density of the load and a coefficient between the total mass of the load and the total volumetric filling of the load.

* * * * *